(12) United States Patent
Stratmann et al.

(10) Patent No.: US 6,798,169 B2
(45) Date of Patent: Sep. 28, 2004

(54) RECHARGEABLE TOOTHBRUSHES WITH CHARGING STATIONS

(75) Inventors: Martin Stratmann, Frankfurt (DE); Peter Trawinski, Weiterstadt (DE)

(73) Assignee: Braun GmbH, Kronberg ( * ) Notice: Subject to any disclaimer, the term of this patent is extended or adjusted under 35 U.S.C. 154(b) by 0 days.

(21) Appl. No.: 10/306,847

(22) Filed: Nov. 21, 2002

(65) Prior Publication Data

US 2003/0085687 A1 May 8, 2003

Related U.S. Application Data

(63) Continuation of application No. PCT/EP01/04280, filed on Apr. 14, 2001.

(30) Foreign Application Priority Data

May 31, 2000 (DE) .......................................... 100 26 859

(51) Int. Cl.⁷ ............................................. H01M 10/46
(52) U.S. Cl. ....................................... 320/114; 320/115
(58) Field of Search ........................... 15/363; D04/101, D04/104; 320/107, 108, 110, 112, 113, 114, 115, 132

(56) References Cited

U.S. PATENT DOCUMENTS

| 4,788,734 | A | * | 12/1988 | Bauer |
| 5,184,959 | A | | 2/1993 | Oryhon et al. |
| 5,544,382 | A | | 8/1996 | Giuliani et al. |
| 5,864,288 | A | * | 1/1999 | Hogan |
| 5,930,858 | A | | 8/1999 | Jung |

FOREIGN PATENT DOCUMENTS

| DE | 40 02 647 A1 | 8/1990 |
| DE | 40 36 479 A1 | 5/1992 |
| DE | 195 44 066 A1 | 5/1997 |
| DE | 297 09 865 U1 | 10/1997 |
| DE | 198 11 676 A1 | 9/1999 |

* cited by examiner

*Primary Examiner*—Edward H. Tso
(74) *Attorney, Agent, or Firm*—Fish & Richardson P.C.

(57) ABSTRACT

An electric toothbrush with a casing has a sensor means and a signal emitting means. The toothbrush can be coupled to a charging station. The sensor means detects the coupling and/or uncoupling of the charging station and the casing and activates the signal emitting means, which then emits signals that are perceptible to the operator.

68 Claims, 2 Drawing Sheets

RECHARGEABLE TOOTHBRUSHES WITH CHARGING STATIONS

This is a continuation of PCT application serial no. PCT/EP01/04280, filed Apr. 14, 2001, which claims priority from German application serial number 10026859.5, filed May 31, 2000.

TECHNICAL FIELD

This invention relates to rechargeable electric toothbrushes with charging stations.

BACKGROUND

Rechargeable electric toothbrushes are generally known and have been well tried and tested in practice. Some of these toothbrushes are equipped with a timer that notifies the operator once a prescribed or recommended cleaning time has passed. Typically, about two minutes are allotted for the cleaning time. If necessary, this cleaning time interval can be subdivided, so that the operator is notified, for example, of the time allotted to clean the lower and upper rows of teeth. After the lapse of the allotted cleaning time, the toothbrush generates an optical or acoustic signal, indicating to the operator that the end of the cleaning interval has been reached.

Usually, electric motor-driven toothbrushes equipped with a battery are placed on a charging station after use, so that the battery can be recharged. At the next time of use, the toothbrush operator removes the toothbrush from the charging station and activates it with an on/off switch. Occasionally, however, some operators of electric motor-driven toothbrushes are unaware of the presence of a timer because, for example, they have not read the operating instructions carefully. Alternatively, the operator may have turned the toothbrush on for only a very short cleaning time, so that the end of the cleaning interval prescribed by the timer is not reached and therefore the signal transmitter does not emit a signal. In such cases, the timer is virtually useless because the operator does not receive any information to the effect that the tooth-cleaning period is insufficient and consequently, that the tooth cleaning itself is also inadequate.

Furthermore, occasionally the signal emitting means or the timer breaks down, even though the electric motor-driven toothbrush is otherwise functioning properly. In these cases, too, the operator does not receive any information about the recommended cleaning time. Regardless, it is also relatively tiresome for the operator to check whether the signal transmitter or the timer is ready for operation.

Finally, it can be difficult to motivate toothbrush operators, especially children, to adequately clean their teeth.

DE 40 36 479 A1 discloses a toothbrush with the aforementioned features. A sensor means detects a coupling between the charging station and the toothbrush casing, and the on/off switch on the toothbrush is moved into the off position. Thus, it is ensured that the electric toothbrush is in the off position while its battery is recharging.

DE 198 11 676 A1 discloses a toothbrush with a device for generating signals by means of a battery.

DE 40 02 647 A1 discloses an electronic toothbrush with a grip. The grip has a light-emitting diode or a device for generating acoustic signals, as well as an electric switch for activation. When the operator grips the brush and brings it into contact with the teeth, a signal that is perceptible to the operator is emitted.

DE 297 09 865 U1 discloses a toothbrush with a signal device for emitting an acoustic signal.

Finally, U.S. Pat. No. 5,184,959 A discloses a bracket for mounting manual toothbrushes. Individual mountings in the bracket are assigned to individual manual toothbrushes having different grip designs. A timing means can be started when the operator removes the manual toothbrush from the bracket.

SUMMARY

In general, the invention features rechargeable electric toothbrushes.

In one aspect, the invention features a teeth-cleaning apparatus. The apparatus includes a charging station that is connectable to a power source and a toothbrush. The toothbrush includes a brush head, a casing with an electric motor for driving the brush head, and a battery for providing power to the electric motor. The toothbrush is couplable to the charging station for charging the battery. Additionally, the toothbrush emits a signal to an operator in response to a change of coupling between the toothbrush and the charging station.

In another aspect, the invention features a teeth-cleaning apparatus. The apparatus includes a toothbrush with a brush head, a casing having an electric motor for driving the brush head, and a battery for providing power to the electric motor. The apparatus further includes a charging station that is connectable to a power source and couplable to the toothbrush for charging the battery. Additionally, the apparatus includes a means for detecting coupling and/or uncoupling between the charging station and the toothbrush, and a means for emitting a signal perceptible to an operator. The signal emitting means is activated by the detecting means upon coupling and/or uncoupling between the charging station and the toothbrush.

In another aspect, the invention features an apparatus that includes a charging station and a toothbrush. After uncoupling of the toothbrush from the charging station, the toothbrush signals to the operator a predetermined length of time.

In another aspect, the invention features an electric motor-driven toothbrush with a casing and a charging station. The toothbrush includes a signal emitting means that, in preferred embodiments, is controlled by a timer. The signal emitting means emits signals perceptible to the operator that inform the operator as to the appropriate duration of teeth-cleaning. Additionally, the toothbrush includes a sensor means that activates the signal emitting means when the toothbrush operator couples and/or uncouples the toothbrush from its charging station.

Because the toothbrush emits signals upon coupling and/or uncoupling with the charging station, even an operator who, for example, has not read the operating instructions and has a tendency to clean his or her teeth for only a very short time receives optical or acoustic information when removing the toothbrush from and/or placing the toothbrush on the charging station.

In some embodiments, the recommended cleaning time of approximately two minutes is divided into two or three cleaning intervals. Thus, the signal emitting means is not only activated upon the uncoupling and/or coupling of the toothbrush with the charging station and at the end of the recommended cleaning time. Rather, the signal emitting means also emits one or more signals during the recommended cleaning time interval.

In some embodiments, the toothbrush does not include a timer. In some such embodiments, the signal emitting means itself is sufficient for emitting perceptible signals. In some such cases, the toothbrush emits perceptible signals only during coupling and/or uncoupling due to activation of the signal emitting means.

In some embodiments, the sensor means is accommodated in the casing, and a charging current or charging voltage is fed to the sensor means as an input variable. Charging can be effected either by an electrical contact between the charging station and toothbrush casing, or inductively (i.e., free from any direct electrical contact). In some cases, the sensor means is implemented with a mechanical contact which acts between the casing and the charging station and is actuated at the time of coupling or uncoupling between the charging station and toothbrush. However, sensing charging voltage or current or a comparable electrical signal may be considered a less expensive approach, and also has the benefit of allowing inductive coupling.

In some embodiments, the sensor means is sensitive to a temporal change in the charging current or charging voltage during the coupling and/or uncoupling of the charging station and casing. When the casing is removed from the charging station, the charging current or charging voltage drops abruptly for a short period. When the casing is returned to the charging station, the charging current or charging voltage increases abruptly. The sensor means evaluates this temporally rapid change in the charging current or charging voltage and uses it to control the signal emitting means. On the other hand, the sensor means does not detect changes in the charging current or charging voltage with a slower temporal variation.

In some embodiments, the transfer of electrical energy from the charging station to the casing, or more precisely, to the battery, takes place inductively, whereby a detector means of a receiver coil is connected downstream in the casing. A transmitter coil is arranged in the charging station itself as a primary coil, to which for example an alternating current of 20 kHz is applied. The receiver coil is arranged in the casing as a secondary coil which receives the electrical energy radiated by the transmitter coil and feeds it to the battery, for example by a charging control means. In some embodiments, the toothbrush casing can be designed to be watertight because of this contactless design. Additionally, the electrical signal sizes on the receiver coil and the charging control means indicate whether the toothbrush is coupled with the charging station. The detector means evaluates changes in these electrical signal sizes from the time standpoint and uses them to control the signal emitting means.

In another embodiment of the invention, the signals emitted by the signal emitting means form an acoustic melody. The acoustic melody can be adapted to suit the individual preferences of the operator. The time period for which the melody plays preferably is between about one second and about ten seconds.

In some cases, a memory means for storing several different signals or signal sequences, in particular, different melodies, can be arranged in the casing. For example, four, eight or even sixteen different signals, signal sequences or melodies can be stored, so that the toothbrush can emit different signals, signal sequences or melodies in succession.

In some embodiments, a random generator means is assigned to the memory means. The random generator means selects and displays or plays one or more signals, signal sequences or melodies when coupling and/or uncoupling is detected, or when a cleaning time interval defined by a timer has ended.

In some embodiments, an optical or acoustic signal transmitter is connected downstream of the signal emitting means. The signal transmitter makes the signals, signal sequences or melodies generated by the signal emitting means perceptible to the operator. If an optical signal transmitter is used, then one or more light-emitting diodes can be provided and controlled individually or in a certain time sequence. If an acoustic signal transmitter is used, then a loudspeaker, a piezoelectric crystal or the electric motor itself can be switched on and off for a short time by a driver stage according to the signals generated by the signal emitting means.

In some cases, the electric motor is connected as a signal transmitter downstream of the signal emitting means, whereby the electric motor at rest is operated as a loudspeaker and reproduces melodies generated by the signal emitting means. Regarding this development, reference is made to German patent application 199 38 670.6, the contents of which are incorporated herein by reference.

Advantages of the current invention include the attraction of toothbrush operators to the toothbrush's acoustic melodies and visual signals. Additionally, the invention appeals to children by emitting signals such as familiar songs in a random sequence. A random sequence of signals motivates children to brush their teeth more regularly and for a longer duration of time. Furthermore, the toothbrush informs operators of an appropriate cleaning time, so that operators are more likely to adequately clean their teeth.

Other aspects, features, and advantages of the invention will become apparent by the following detailed description, the drawings, and the claims.

DETAILED DESCRIPTION OF DRAWINGS

Figure 1:
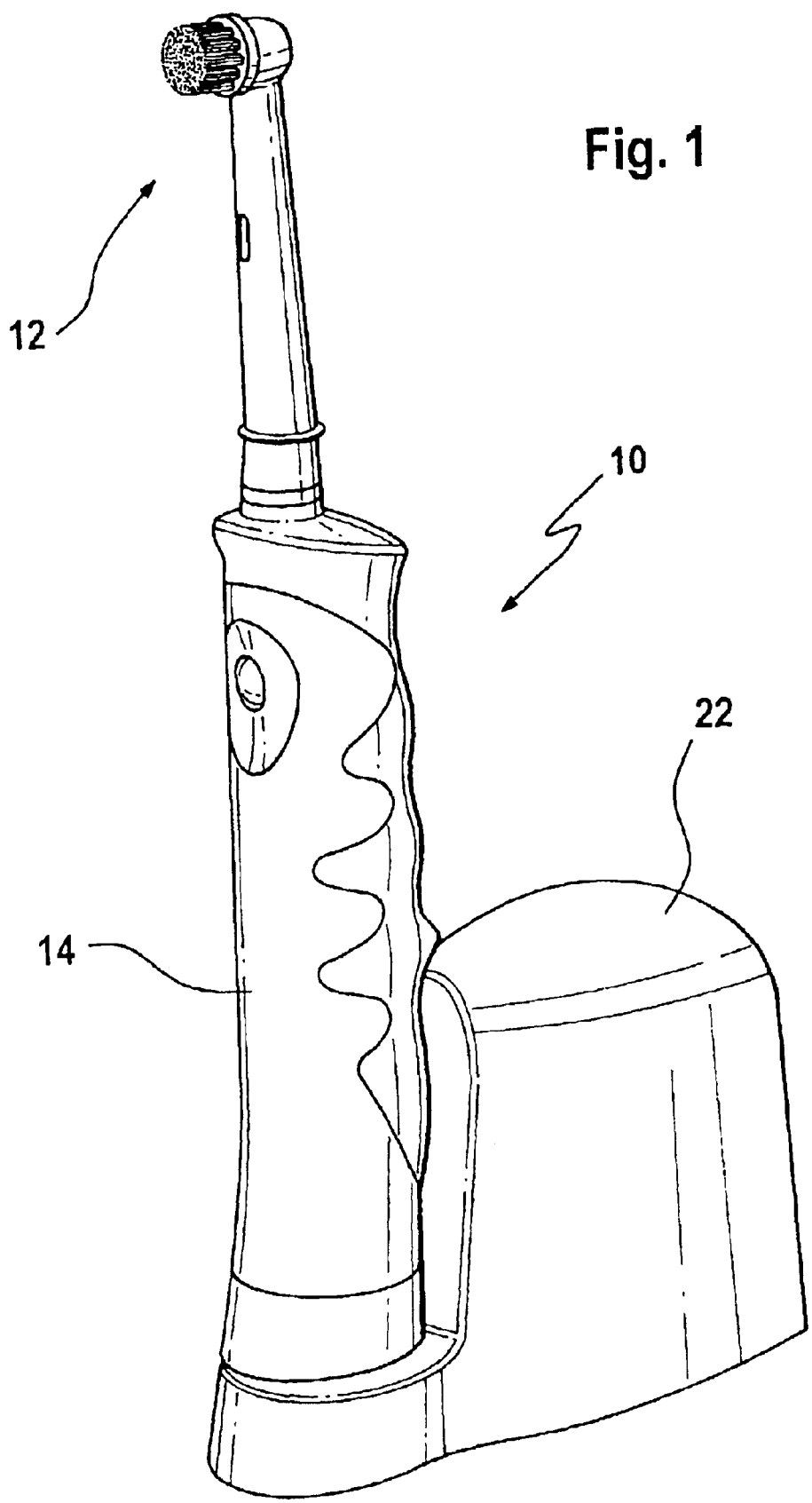
FIG. 1 is a diagrammatic view of an electric motor-driven toothbrush with a charging station, according to one embodiment of the invention.
Figure 2:
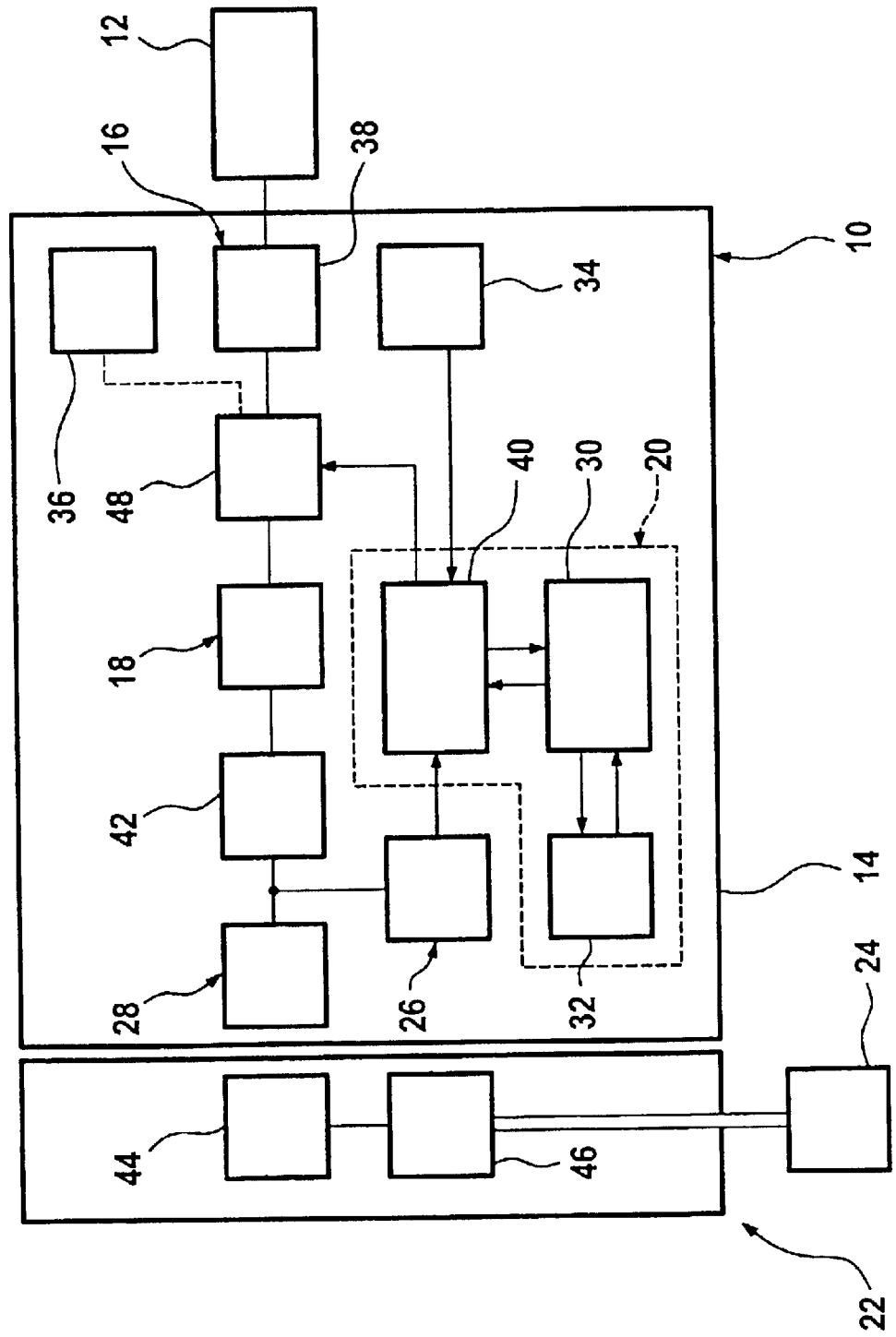
FIG. 2 is a schematic illustration of a toothbrush with a charging station according to one embodiment of the invention.

Referring to FIGS. 1 and 2, a toothbrush 10 with a brush head 12 and a casing 14 is shown. Referring to FIG. 2, casing 14 includes an electric motor 16 that drives brush head 12, and a battery 18 that supplies power to electric motor 16. Toothbrush 10 has a signal emitting means 20 as well as a timer 34. Signal emitting means 20 preferably controls a signal transmitter 36 or more preferably, a loudspeaker 38, via a driver stage 48. Signal transmitter 36 preferably is a light-emitting diode, a piezoelectric crystal or the like. Loudspeaker 38 is formed by electric motor 16 when electric motor 16 is operated as a loudspeaker during rest phases.

When not in use, toothbrush 10 can be coupled with a charging station 22. Charging station 22 is connected to an electrical outlet 24. Charging station 22 has a charging control stage 46 that is connectable to electrical outlet 24, as well as a connected transmitter coil 44. When the operator couples toothbrush 10 to charging station 22, transmitter coil 44 is inductively coupled with a receiver coil 28 arranged in casing 14, so that electrical energy is transferred from transmitter coil 44 to receiver coil 28, without transmitter coil 44 and receiver coil 28 being in contact. A charging control means 42 is connected to receiver coil 28. Downstream of charging control means 42, battery 18, driver stage 48 and electric motor 16 are connected. The output signals from receiver coil 28 and signals from charging control means 42 are fed to sensor means 26. Sensor means 26 is connected to signal emitting means 20.

Signal emitting means 20 has a memory means 30, a random generator means 32 and a generator 40. Generator 40 is connected to driver stage 48.

Sensor means 26 detects a coupling and/or uncoupling between charging part 22 and casing 14, and then activates signal emitting means 20. An electrical signal is fed as an input variable to sensor means 26, the electrical signal being a measure of the charging current or charging voltage. Sensor means 26 is sensitive to the temporal change in the charging current or charging voltage during the coupling and/or uncoupling of charging part 22 and casing 14.

The signals generated by signal emitting means 20 or emitted by signal transmitter 36, loudspeaker 38, or electric motor 16 are preferably one or more acoustic melodies. Memory means 30 can store several different acoustic signal sequences. Random generator means 32 randomly selects one of the several signal sequences, and the selected signal sequence or melody is then emitted by toothbrush 10 as the next signal. Generator 40 ensures that the preferably digitally-stored signals or signal sequences are fed in the correct time sequence to signal transmitter 36, loudspeaker 38, or electric motor 16.

Signal emitting means 20 is activated when, for example, toothbrush 10 is removed from charging station 22. In this case, sensor means 26 detects an abrupt change in the charging current or charging voltage of receiver coil 28 or charging control means 42, and accordingly activates signal emitting means 20. Toothbrush 10 then plays, for example, a short melody. When toothbrush 10 is activated for teeth-cleaning, timer 34 is also activated. Timer 34 again activates signal emitting means 20 after the lapse of a time interval of, for example, approximately two minutes, e.g. approximately one minute, e.g., approximately thirty seconds. Random generator means 32 then selects a further melody, so that the operator is informed about the lapse of a cleaning interval or a cleaning sub-interval. At the end of the cleaning procedure, toothbrush 10 is deactivated and again placed or plugged back on charging station 22. If need be, signal emitting means 20 can be activated again via sensor means 26, so that a further signal sequence or the same melody is emitted by toothbrush 10. Generally, however, it should be sufficient for toothbrush 10 to play a short melody only when it is removed from charging station 22.

What is claimed is:

1. An apparatus for cleaning teeth, the apparatus comprising:
    a charging station that is connectable to a power source; and
    a toothbrush including
        a brush head,
        a casing having an electric motor for driving the brush head, and
        a battery for providing power to the electric motor, wherein the toothbrush is couplable to the charging station for charging the battery, and wherein the electric motor emits an audible signal to an operator in response to a change of coupling between the toothbrush and the charging station.

2. The apparatus of claim 1, wherein the toothbrush includes a sensor responsive to coupling between the toothbrush and the charging station.

3. The apparatus of claim 2, wherein the sensor causes the electric motor to emit the audible signal upon coupling and/or uncoupling between the charging station and the toothbrush.

4. The apparatus of claim 3, wherein the sensor is sensitive to a temporal change in electrical signals during the coupling and/or uncoupling of the charging station and the toothbrush.

5. The apparatus of claim 3, wherein the sensor is disposed within the casing.

6. The apparatus of claim 5, wherein the sensor is responsive to a charging current.

7. The apparatus of claim 6, wherein the sensor is sensitive to a temporal change in electrical signals during coupling and/or uncoupling of the charging station and the toothbrush.

8. The apparatus of claim 5, wherein the sensor is responsive to a charging voltage.

9. The apparatus of claim 8, wherein the sensor is sensitive to a temporal change in electrical signals during coupling and/or uncoupling of the charging station and the toothbrush.

10. The apparatus of claim 3, wherein the charging station and the toothbrush are inductively couplable, and wherein the toothbrush includes a receiver coil responsive to inductive coupling between the toothbrush and the charging station.

11. The apparatus of claim 3, wherein the audible signal emitted by the electric motor comprises an acoustic melody.

12. The apparatus of claim 3, wherein the casing includes a device for storing different signals or signal sequences.

13. The apparatus of claim 12, wherein the signals or signal sequences comprise different acoustic melodies.

14. The apparatus of claim 1, wherein the electric motor signals to the operator a predetermined length of time after uncoupling of the toothbrush from the charging station.

15. An apparatus for cleaning teeth comprising:
    a toothbrush including
        a brush head,
        a casing having an electric motor for driving the brush head, and
        a battery for providing power to the electric motor;
    a charging station that is connectable to a power source and couplable to the toothbrush for charging the battery; and
    a means for sensing coupling and/or uncoupling between the charging station and the toothbrush,
    wherein the electric motor is activated by the sensing means to emit an audible signal perceptible to an operator upon coupling and/or uncoupling between the charging station and the toothbrush.

16. The apparatus of claim 15, wherein the casing further comprises a means for storing different signals or signal sequences.

17. The apparatus of claim 16, wherein the signals or signal sequences comprise different acoustic melodies.

18. The apparatus of claim 15, wherein the electric motor emits a signal to the operator a predetermined length of time after uncoupling of the toothbrush from the charging station.

19. The apparatus of claim 15, wherein the sensing means is sensitive to a temporal change in electrical signals during the coupling and/or uncoupling of the charging station and the toothbrush.

20. The apparatus of claim 15, wherein the sensing means is disposed within the casing.

21. The apparatus of claim 20, wherein the sensing means is responsive to a charging current.

22. The apparatus of claim 21, wherein the sensing means is sensitive to a temporal change in electrical signals during the coupling and/or uncoupling of the charging station and the toothbrush.

23. The apparatus of claim 20, wherein the sensing means is responsive to a charging voltage.

24. The apparatus of claim 23, wherein the sensing means is sensitive to a temporal change in electrical signals during the coupling and/or uncoupling of the charging station and the toothbrush.

25. The apparatus of claim 15, wherein the charging station and the toothbrush are inductively couplable, and wherein the toothbrush includes a receiver coil responsive to inductive coupling between the toothbrush and the charging station.

26. The apparatus of claim 15, wherein the audible signal emitted by the electric motor comprises an acoustic melody.

27. An apparatus for cleaning teeth, the apparatus comprising:
   a charging station that is connectable to a power source; and
   a toothbrush that is couplable to the charging station for charging a battery, the toothbrush including
      a brush head,
      a casing having an electric motor for driving the brush head,
      a battery for providing power to the electric motor, and
      a sensor that is responsive to coupling between the toothbrush and the charging station,
   wherein the sensor causes the electric motor to emit an audible signal to an operator after a time interval following uncoupling between the toothbrush and the charging station.

28. The apparatus of claim 27, wherein the audible signal is an acoustic melody.

29. An apparatus for cleaning teeth, the apparatus comprising:
   a toothbrush including
      a brush head,
      a casing having an electric motor for driving the brush head,
      a battery for providing power to the electric motor, and
      disposed within the casing, a means for sensing coupling and/or uncoupling between the toothbrush and the charging station, the sensing means being responsive to a charging current;
   a charging station that is connectable to a power source and couplable to the toothbrush for charging the battery; and
   a means for emitting a signal perceptible to an operator,
   wherein the sensing means causes the emitting means to emit the signal upon coupling and/or uncoupling between the charging station and the toothbrush.

30. The apparatus of claim 29, wherein the sensing means is sensitive to a temporal change in electrical signals during the coupling and/or uncoupling of the charging station and the toothbrush.

31. The apparatus of claim 29, wherein the signal emitted by the emitting means is an audible signal.

32. The apparatus of claim 29, wherein the audible signal is an acoustic melody.

33. An apparatus for cleaning teeth, the apparatus comprising:
   a charging station that is connectable to a power source; and
   a toothbrush that is couplable to the charging station for charging a battery, the toothbrush including
      a brush head,
      a casing having an electric motor for driving the brush head,
      the battery for providing power to the electric motor, and
      a sensor that is disposed within the casing and that is responsive to a charging voltage,
   wherein the sensor causes the toothbrush to emit a signal to an operator upon coupling and/or uncoupling between the charging station and the toothbrush.

34. The apparatus of claim 33, wherein the sensor is sensitive to a temporal change in electrical signals during coupling and/or uncoupling of the charging station and the toothbrush.

35. The apparatus of claim 33, wherein the signal emitted by the toothbrush is an audible signal.

36. The apparatus of claim 35, wherein the audible signal is an acoustic melody.

37. The apparatus of claim 33, wherein the charging station and the toothbrush are inductively couplable, and wherein the toothbrush includes a receiver coil responsive to inductive coupling between the toothbrush and the charging station.

38. The apparatus of claim 33, wherein the casing includes a device for storing different signals or signal sequences.

39. The apparatus of claim 38, wherein the signals or signal sequences comprise different acoustic melodies.

40. The apparatus of claim 33, wherein the electric motor signals to the operator a predetermined length of time after uncoupling of the toothbrush from the charging station.

41. An apparatus for cleaning teeth, the apparatus comprising:
   a toothbrush including
      a brush head,
      a casing having an electric motor for driving the brush head,
      a battery for providing power to the electric motor, and
      disposed within the casing, a sensing means for sensing coupling and/or uncoupling between the toothbrush and the charging station, the sensing means being responsive to a charging voltages;
   a charging station that is connectable to a power source and couplable to the toothbrush for charging the battery; and
   a means for emitting a signal perceptible to an operator,
   wherein the sensing means causes the emitting means to emit the signal upon coupling and/or uncoupling between the charging station and the toothbrush.

42. The apparatus of claim 41, wherein the sensing means is sensitive to a temporal change in electrical signals during the coupling and/or uncoupling of the charging station and the toothbrush.

43. The apparatus of claim 41, wherein the signal emitted by the emitting means is an audible signal.

44. The apparatus of claim 43, wherein the audible signal is an acoustic melody.

45. An apparatus for cleaning teeth, the apparatus comprising:
   a toothbrush including
      a brush head,
      a casing having an electric motor for driving the brush head, and
      a battery for providing power to the electric motor;
   a charging station that is connectable to a power source and couplable to the toothbrush for charging the battery; and
   a means for sensing coupling and/or uncoupling between the toothbrush and the charging station, wherein, after a time interval following uncoupling of the toothbrush and the charging station, the sensing means causes the motor to emit an audible signal perceptible to an operator.

46. The apparatus of claim 45, wherein the audible signal is an acoustic melody.

47. An apparatus for cleaning teeth, the apparatus comprising:
a charging station that is connectable to a power source; and
a toothbrush that is couplable to the charging station for charging a battery, the toothbrush including
a brush head,
a casing having an electric motor for driving the brush head,
the battery for providing power to the electric motor, and
a sensor that is disposed within the casing and that is responsive to a charging current,
wherein the sensor causes the toothbrush to emit a signal to an operator upon coupling and/or uncoupling between the charging station and the toothbrush.

48. The apparatus of claim 47, wherein the electric motor signals to the operator a predetermined length of time after uncoupling of the toothbrush from the charging station.

49. The apparatus of claim 47, wherein the signal emitted by the toothbrush is an audible signal.

50. The apparatus of claim 49, wherein the audible signal is an acoustic melody.

51. The apparatus of claim 47, wherein the sensor is sensitive to a temporal change in electrical signals during coupling and/or uncoupling of the charging station and the toothbrush.

52. The apparatus of claim 47, wherein the charging station and the toothbrush are inductively couplable, and wherein the toothbrush includes a receiver coil responsive to inductive coupling between the toothbrush and the charging station.

53. The apparatus of claim 47, wherein the casing includes a device for storing different signals or signal sequences.

54. The apparatus of claim 53, wherein the signals or signal sequences comprise different acoustic melodies.

55. An apparatus comprising a charging station and a toothbrush including an electric motor, wherein the electric motor provides an audible signal to an operator a predetermined length of time after uncoupling of the toothbrush from the charging station.

56. The apparatus of claim 55, wherein the toothbrush includes a sensor responsive to coupling between the toothbrush and the charging station.

57. The apparatus of claim 56, wherein the sensor causes the electric motor to emit the audible signal upon coupling and/or uncoupling between the charging station and the toothbrush.

58. The apparatus of claim 57, wherein the sensor is sensitive to a temporal change in electrical signals during the coupling and/or uncoupling of the charging station and the toothbrush.

59. The apparatus of claim 57, wherein the charging station and the toothbrush are inductively couplable, and wherein the toothbrush includes a receiver coil responsive to inductive coupling between the toothbrush and the charging station.

60. The apparatus of claim 57, wherein the audible signal emitted by the electric motor comprises an acoustic melody.

61. The apparatus of claim 57, further comprising a casing that includes a device for storing different signals or signal sequences.

62. The apparatus of claim 61, wherein the signals or signal sequences comprise different acoustic melodies.

63. The apparatus of claim 57, further comprising a casing.

64. The apparatus of claim 63, wherein the sensor is disposed within the casing.

65. The apparatus of claim 64, wherein the sensor is responsive to a charging current.

66. The apparatus of claim 65, wherein the sensor is sensitive to a temporal change in electrical signals during coupling and/or uncoupling of the charging station and the toothbrush.

67. The apparatus of claim 64, wherein the sensor is responsive to a charging voltage.

68. The apparatus of claim 67, wherein the sensor is sensitive to a temporal change in electrical signals during coupling and/or uncoupling of the charging station and the toothbrush.

* * * * *

UNITED STATES PATENT AND TRADEMARK OFFICE
CERTIFICATE OF CORRECTION

PATENT NO. : 6,798,169 B2  
DATED : September 28, 2004  
INVENTOR(S) : Martin Stratmann and Peter Trawinski It is certified that error appears in the above-identified patent and that said Letters Patent is hereby corrected as shown below:

Column 8,
Line 39, delete "voltages;" and insert -- voltage; --

Signed and Sealed this

Fifteenth Day of February, 2005

JON W. DUDAS  
*Director of the United States Patent and Trademark Office*